United States Patent
Cho et al.

(10) Patent No.: US 9,448,229 B2
(45) Date of Patent: Sep. 20, 2016

(54) KIT FOR MONITORING IMMUNE STATUS AFTER TRANSPLANT AND METHOD FOR MONITORING IMMUNE STATUS USING SAME

(71) Applicant: THE CATHOLIC UNIVERSITY OF KOREA INDUSTRY-ACADEMIC COOPERATION FOUNDATION, Seoul (KR)

(72) Inventors: Mi-La Cho, Seoul (KR); Chul-Woo Yang, Seoul (KR); Jong-Young Choi, Seoul (KR); Joo-Yeon Jhun, Seoul (KR); Hee-Yeon Kim, Seoul (KR); Jae-Kyeong Byun, Jecheon-si (KR); Ye-Been Yim, Seoul (KR); Byung-Ha Chung, Seoul (KR); Kyoung-Woon Kim, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 18 days.

(21) Appl. No.: 14/536,359

(22) Filed: Nov. 7, 2014

(65) Prior Publication Data
US 2015/0051108 A1  Feb. 19, 2015

Related U.S. Application Data

(63) Continuation-in-part of application No. PCT/KR2012/011293, filed on Dec. 21, 2012.

(30) Foreign Application Priority Data

May 11, 2012  (KR) .......... 10-2012-0050181

(51) Int. Cl.
*G01N 33/50* (2006.01)
*G01N 33/569* (2006.01)
*G01N 33/68* (2006.01)

(52) U.S. Cl.
CPC .... *G01N 33/5091* (2013.01); *G01N 33/56966* (2013.01); *G01N 33/56972* (2013.01); *G01N 33/56977* (2013.01); *G01N 33/6866* (2013.01); *G01N 33/6869* (2013.01); *G01N 2333/57* (2013.01); *G01N 2800/245* (2013.01)

(58) Field of Classification Search
CPC ............... G01N 33/5091; G01N 33/56966; G01N 33/56972; G01N 33/6866; G01N 33/6869; G01N 33/56977
See application file for complete search history.

(56) References Cited

U.S. PATENT DOCUMENTS

| | | | |
|---|---|---|---|
| 2007/0082356 A1 | 4/2007 | Strom et al. | |
| 2007/0202085 A1 | 8/2007 | Hu et al. | |
| 2010/0190166 A1 | 7/2010 | Halloran et al. | |
| 2011/0212100 A1* | 9/2011 | Keller ................ | A61K 31/517 424/158.1 |

FOREIGN PATENT DOCUMENTS

| | | |
|---|---|---|
| KR | 10-2010-0055390 | 5/2010 |
| KR | 10-2010-0094997 | 8/2010 |

OTHER PUBLICATIONS

Penna et al. Impact of treatment on regulatory CD4+ T lymphocytes, TH17 and cytokines in patients with hodgkin's lymphoma. Blood 122 (21): 21 Abstract No. 1756 (Oct. 21, 2013). Abstract.*
Nakagiri et al. Th17 lymphocyte proportion increased in animal model of bronchiolitis obliterans after lung transplantation. Journal of Heart and Lung Transplantation, 28 (2): Suppl. 1, pp. S172. Abstract No. 304 (Feb. 2009), Abstract.*

* cited by examiner

*Primary Examiner* — Gail R Gabel
(74) *Attorney, Agent, or Firm* — Joseph Hyosuk Kim; JHK Law (57) ABSTRACT

The present invention relates to a method and a kit for monitoring an immune status after transplant. The kit for monitoring an immune status after transplant and the method for monitoring an immune status of an individual after transplant as provided in the present invention make it easy and accurate to determine an immune status in the individual after transplant and thus have an effect of reducing overuse of an immunosuppressive agent prescribed after transplant and also have an effect of conveniently managing an immune status of each patient.

1 Claim, 3 Drawing Sheets

KIT FOR MONITORING IMMUNE STATUS AFTER TRANSPLANT AND METHOD FOR MONITORING IMMUNE STATUS USING SAME

TECHNICAL FIELD

The present invention relates to a novel diagnostic kit capable of determining timing for reducing a dosage of an immunosuppressive agent and determining whether or not to administer the immunosuppressive agent by monitoring an immune status of a patient after transplant.

BACKGROUND ART

Immunity refers to a self-defense system of a living body against all exogenous high molecular substances (antigens) which invade or enter the living body. Lymphocytes, as a critical component of an immune system, are white blood cells which originate from the bone marrow and circulate in blood and migrate to lymphoid tissues or organs, particularly, lymph nodes, the spleen and the tonsils. As cells involved in immune reactions, B cells, when stimulated by a suitable antigen, rapidly proliferate to form clones from which specific antibodies (immunoglobulin) for neutralizing the antigen are produced. Circulating in the body fluid, the antibodies produced by B cells function to perform humoral immunity. Further, T cells are produced in the thymus and migrate to lymphoid tissues, and are responsible for cell-mediated immunity directly attacking antigens.

One of the most important characteristics of a normal individual is an ability to recognize, respond to, and eliminate non-self-antigens, while not responding harmfully to self-antigens. This non-responding of a living organism to self-antigens is called "immunologic unresponsiveness" or "tolerance".

When this ability to induce or maintain self-tolerance is troubled, an immune reaction occurs even to the self-antigens, leading to a phenomenon of attacking self-tissues, and autoimmune disease such as multiple sclerosis, diabetes mellitus type 1, rheumatoid arthritis, Hashimoto's thyroiditis is developed in this process. Also, an immune rejection response occurs after a surgical procedure such as transplant.

Meanwhile, an immune rejection response of a recipient to the transplanted cells or organs has to be dealt with, in order to ensure successful organ transplant. T cells are the major mediator of transplant rejection. That is, an immune reaction is induced, leading to transplant rejection, as the T cell receptor perceives the major histocompatibility complex (MHC) expressed on the graft.

Due to recent development of surgical procedure and HLA typing and development of immunosuppressive agents, a success rate of transplant has increased. However, a death rate is still high due to an immune rejection response and immunosuppressive agents. Therefore, there has been a demand for development of novel, effective and safe immunosuppressive agents.

The common object of all the conventional immunosuppressive agents is to suppress T cell-mediated immunity to a graft. Clinically, in order to suppress T cell-mediated acute rejection after clinical transplant, a nonspecific immunosuppressive agent is administered every day (Pirsch, J. D., curr. opin. organ. transplant., 2, 76 to 81, 1997). Examples of immunosuppressive agents generally used include azathioprine and mycophenolate mofetil that contain glucocorticosteroids to inhibit DNA synthesis and thus to suppress T cell proliferation, and cyclosporine A and tacrolimus as calcineurin inhibitors. These drugs have been improved a lot in overcoming an immune rejection response of an organ transplant patient, but they have problems including a temporary therapeutic effect and high toxicity.

Therefore, although it is important to develop an immunosuppressive agent for suppressing transplant rejection, at this point in time when an immunosuppressive agent having a clear therapeutic effect needs to be further developed, the most effective and fastest method for minimizing side effects caused by administration of an immunosuppressive agent is to reduce a dosage of the immunosuppressive agent. However, if a reduced dosage of the immunosuppressive agent is administered to an organ transplant patient due to fear of any side effect without any criteria, there may be an increase in pain due to transplant rejection. Thus, if a method of reducing a dosage of an immunosuppressive agent with respect to a patient in a good immune status and treating a patient, who is not in a good immune status, with an immunosuppressive agent in the same amount as used previously by checking an immune status in an organ transplant patient with general standards is developed, it is possible to reduce pain of the patient caused by the immunosuppressive agent.

As such, immunosuppressive agents, which have been used for a transplant and administered to many patients with immune diseases can cause various side effects in the body, and particularly, as for a patient after surgery such as transplant, there is no alternative but to prescribe an immunosuppressive agents to suppress an immune rejection response even after considering that side effects inevitably occur.

However, since an immunosuppressive agent without any side effect cannot be developed so far, the best method for reducing side effects caused by immunosuppressive agents is to reduce a dosage at this point in time. However, any guideline on timing for reducing a dosage of a drug and the extent of the reduction has not been provided yet.

DISCLOSURE

Technical Problem

The present invention is directed to providing a kit for monitoring an immune status after transplant, the kit including a substance for measuring Th17 cells, Treg cells, Th1 cells, CD8EM (CD8 effect memory) IFN-γ positive cells, and CD8CM (CD8 central memory) IFN-γ positive cells.

The present invention is also directed to providing a method for monitoring an immune status of an individual after transplant, the method including: (a) a step of respectively measuring cell counts of Th17 cells, Treg cells, Th1 cells, CD8EM IFN-γ positive cells, and CD8CM IFN-γ positive cells in peripheral blood of the individual receiving a transplant; and (b) a step of respectively calculating cell count ratios of the Treg cells, the Th1 cells, the CD8EM IFN-γ positive cells, and the CD8CM IFN-γ positive cells to the Th17 cells by respectively dividing the cell count values of the Treg cells, the Th1 cells, the CD8EM IFN-γ positive cells, and the CD8CM IFN-γ positive cells by the cell count value of the Th17 cells.

Technical Solution

One aspect of the present invention provides a kit for monitoring an immune status after transplant, the kit including a substance for measuring Th17 cells, Treg cells, Th1 cells, CD8EM (CD8 effect memory) IFN-γ positive cells, and CD8CM (CD8 central memory) IFN-γ positive cells.

In an exemplary embodiment of the present invention, the measuring may be carried out: for the Th17 cells, by using an antibody to IL-17 to measure an amount of the IL-17; for the Treg cells, by using a Foxp3 antibody to measure an amount of Foxp3; for the Th1 cells, by using an antibody to interferon gamma (IFN-γ) to measure an amount of the IFN-γ; for the CD8EM IFN-γ positive cells, by using an anti-human CD8 APC, anti-human CD45RA FITC, anti-human CCR7, or anti-human IFN-γ PE antibody to measure an amount of IFN-γ of a CD8EM T cell; and for the CD8CM IFN-γ positive cells, by using an anti-human CD8 APC, anti-human CD45RA FITC, anti-human CCR7, or anti-human IFN-γ PE antibody to measure an amount of IFN-γ of a CD8CM T cell.

Another aspect of the present invention provides a method for monitoring an immune status of an individual after transplant, the method including: (a) a step of respectively measuring cell counts of Th17 cells, Treg cells, Th1 cells, CD8EM IFN-γ positive cells, and CD8CM IFN-γ positive cells in peripheral blood of the individual receiving a transplant; and (b) a step of respectively calculating cell count ratios of the Treg cells, the Th1 cells, the CD8EM IFN-γ positive cells, and the CD8CM IFN-γ positive cells to the Th17 cells by respectively dividing the cell count values of the Treg cells, the Th1 cells, the CD8EM IFN-γ positive cells, and the CD8CM IFN-γ positive cells by the cell count value of the Th17 cells.

In an exemplary embodiment of the present invention, in the step (a), the measuring cell counts may be carried out: for the Th17 cells, by using an antibody to IL-17 to measure an amount of the IL-17; for the Treg cells, by using a Foxp3 antibody to measure an amount of Foxp3; for the Th1 cells, by using an antibody to IFN-γ to measure an amount of the IFN-γ; for the CD8EM IFN-γ positive cells, by using an anti-human CD8 APC, anti-human CD45RA FITC, anti-human CCR7, or anti-human IFN-γ PE antibody to measure an amount of IFN-γ of a CD8EM T cell; and for the CD8CM IFN-γ positive cells, by using an anti-human CD8 APC, anti-human CD45RA FITC, anti-human CCR7, or anti-human IFN-γ PE antibody to measure an amount of IFN-γ of a CD8CM T cell.

In an exemplary embodiment of the present invention, the method may further include a step of prescribing a reduced dosage of an immunosuppressive agent to the individual after transplant or determining that the immunosuppressive agent does not need to be administered when each cell count ratio of the Treg cells, the Th1 cells, the CD8EM IFN-γ positive cells, and the CD8CM IFN-γ positive cells to the Th17 cells is equal to or higher than 1.

In an exemplary embodiment of the present invention, the method may further include a step of determining that a dosage of an immunosuppressive agent to the individual after transplant should not be reduced when each cell count ratio of the Treg cells, the Th1 cells, the CD8EM IFN-γ positive cells, and the CD8CM IFN-γ positive cells to the Th17 cells is less than 1.

In an exemplary embodiment of the present invention, the immunosuppressive agent may be a calcineurin inhibitor, and preferably, the reduced dosage of an immunosuppressive agent may be in an amount of 75 to 50% based on 100% of an initial dosage of the immunosuppressive agent, but is not limited thereto.

Advantageous Effects

The present invention relates to a kit for monitoring an immune status after transplant, the kit including a substance for measuring Th17 cells, Treg cells, Th1 cells, CD8EM IFN-γ positive cells, and CD8CM IFN-γ positive cells, and a method for monitoring an immune status of an individual after transplant, the method including: (a) a step of respectively measuring cell counts of Th17 cells, Treg cells, Th1 cells, CD8EM IFN-γ positive cells, and CD8CM IFN-γ positive cells in peripheral blood of the individual receiving a transplant; and (b) a step of respectively calculating cell count ratios of the Treg cells, the Th1 cells, the CD8EM IFN-γ positive cells, and the CD8CM IFN-γ positive cells to the Th17 cells by respectively dividing the cell count values of the Treg cells, the Th1 cells, the CD8EM IFN-γ positive cells, and the CD8CM IFN-γ positive cells by the cell count value of the Th17 cells. The kit for monitoring an immune status after transplant and the method for monitoring an immune status of an individual after transplant as provided in the present invention make it easy and accurate to determine an immune status in the individual after transplant and thus have an effect of reducing overuse of an immunosuppressive agent prescribed after transplant and also have an effect of conveniently managing an immune status of each patient.

BEST MODES OF THE INVENTION

The present invention relates to a new kit for monitoring an immune status, and the kit is capable of monitoring an immune status of organ transplant patients. To be more specific, the present invention provides a kit for monitoring an immune status after transplant, the kit including a substance for measuring Th17 cells, Treg cells, Th1 cells, CD8EM (CD8 effect memory) IFN-γ positive cells, and CD8CM (CD8 central memory) IFN-γ positive cells.

In the present invention, as a marker which can be used to monitor an immune status after transplant, the Th17 cells, the Treg cells, the Th1 cells, the CD8EM IFN-γ positive cells, and the CD8CM IFN-γ positive cells may be used, and more preferably, an immune status can be monitored by measuring a cell count of each of the Th17 cells, the Treg cells, the Th1 cells, the CD8EM IFN-γ positive cells, and the CD8CM IFN-γ positive cells from a nuclear cell in peripheral blood obtained from an individual after transplant.

The inventors of the present invention found a marker which can be used to monitor an immune status after transplant for managing prognosis after transplant, can be applied to each organ transplant patient, and can also reduce an overdose of an immunosuppressive agent after transplant.

According to an exemplary embodiment of the present invention, with respect to nuclear cells in peripheral blood collected from the liver transplant patients in a good immune status and the liver transplant patients in a bad immune status while reducing a dose of an immunosuppressive agent administered, for the Th17 cells, an amount of the IL-17 was measured by using an antibody to IL-17; for the Treg cells, an amount of Foxp3 was measured by using a Foxp3 antibody; for the Th1 cells, an amount of the IFN-γ was measured by using an antibody to IFN-γ; for the CD8EM IFN-γ positive cells, an amount of IFN-γ of a CD8EM T cell was measured by using an anti-human CD8 APC, anti-human CD45RA FITC, anti-human CCR7, or anti-human IFN-γ PE antibody; and for the CD8CM IFN-γ positive cells, an amount of IFN-γ of a CD8CM T cell was measured by using an anti-human CD8 APC, anti-human CD45RA FITC, anti-human CCR7, or anti-human IFN-γ PE antibody.

Figure 1:
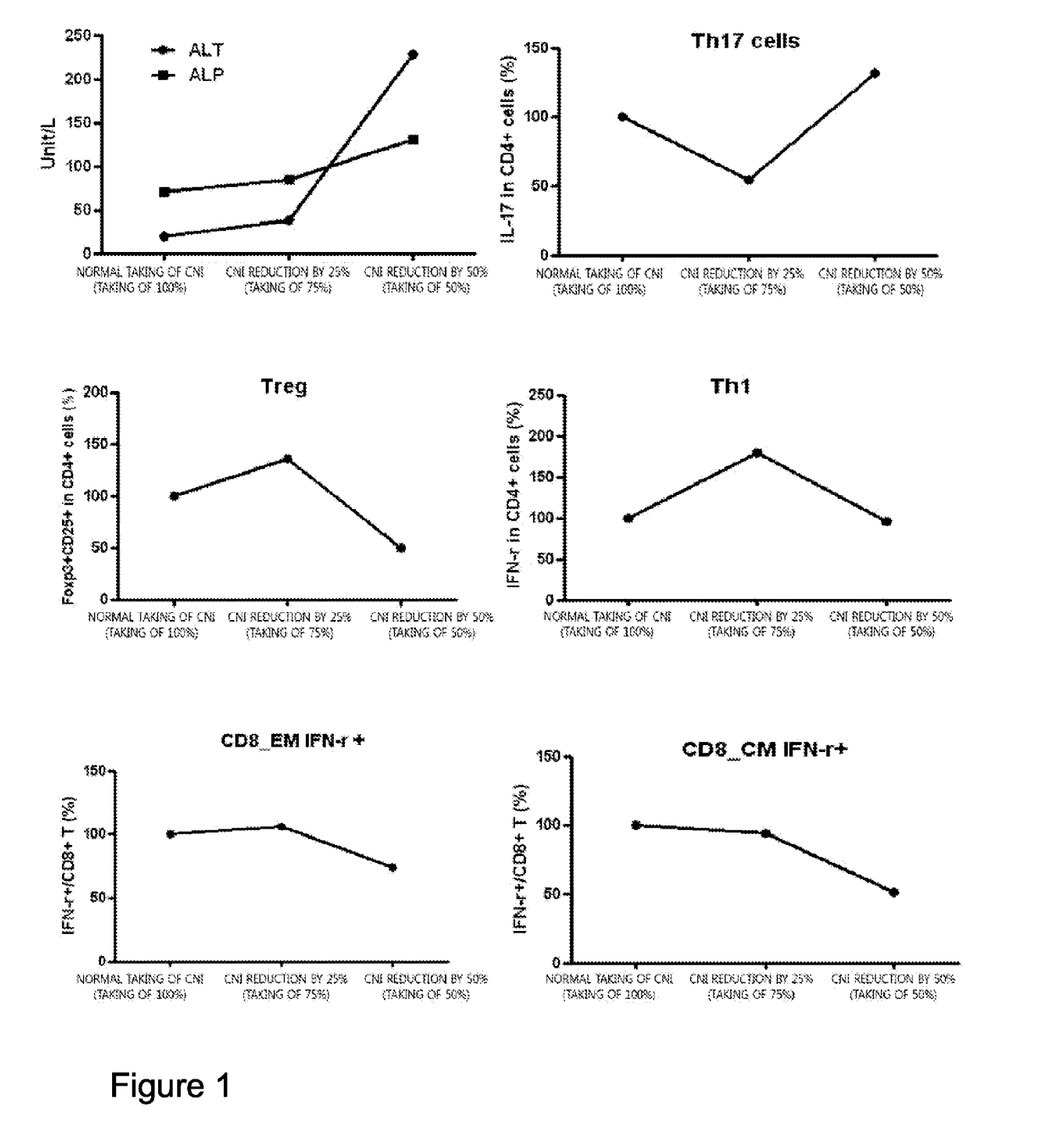
FIG. 1 is a graph illustrating changes in cell counts of Th17 cells, Treg cells, Th1 cells, CD8EM IFN-γ positive cells, and CD8CM IFN-γ positive cells measured while a dosage of an immunosuppressive agent to be administered to a mononuclear cell in peripheral blood obtained from a patient in a bad immune status among liver transplant patients according to an exemplary embodiment of the present invention.

According to a result of the measurement, it was observed that as for the group in a bad immune status after transplant and in need of being continuously administered with an immunosuppressive agent in the same amount as an initial dose, the cell count of the Th17 cells as pathogenic cells increased, whereas the respective cell counts of the Treg cells, the Th1 cells, the CD8EM IFN-γ positive cells, and the CD8CM IFN-γ positive cells decreased (refer to FIG. 1).

Figure 3:
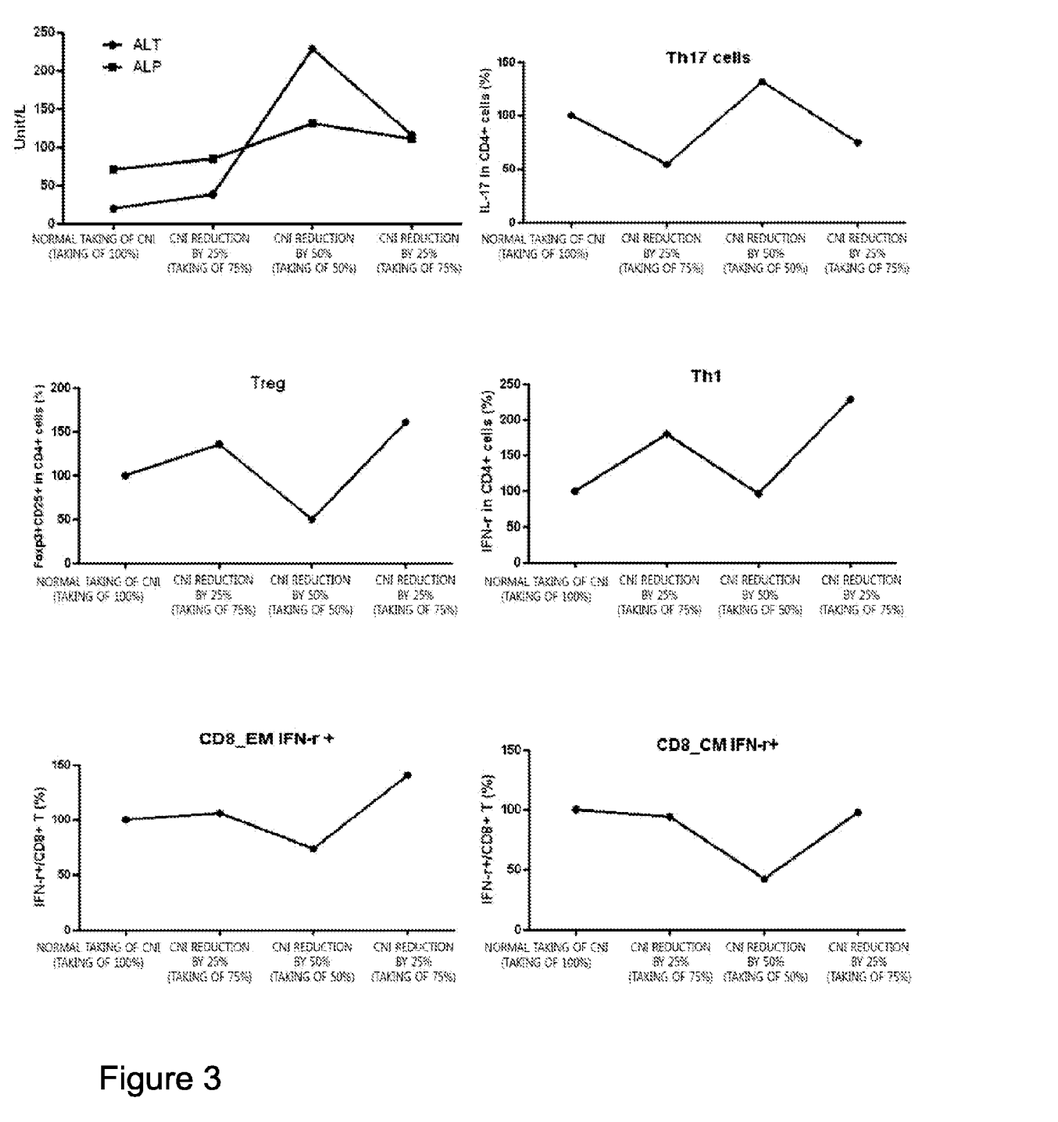
FIG. 3 illustrates a result of checking whether or not an immune status is recovered when a dosage of an immunosuppressive agent in an experimental group of FIG. 1 is reduced to 50% and then increased to 75% based on changes in cell counts of Th17 cells, Treg cells, Th1 cells, CD8EM IFN-γ positive cells, and CD8CM IFN-γ positive cells.

However, it was observed that as for the group in a good immune status and not in need of being administered with an immunosuppressive agent or as being allowed to be reduced in a dose of an immunosuppressive agent, the respective cell counts of the Treg cells, the Th1 cells, the CD8EM IFN-γ positive cells, and the CD8CM IFN-γ positive cells were maintained or increased, whereas due to the reduced dose of the immunosuppressive agent, the cell count the Th17 cells as pathogenic cells slightly increased but to a small degree (refer to FIG. 3).

Therefore, the inventors of the present invention found that as markers which can be used to monitor an immune status of a patient after transplant, the Th17 cells, the Treg cells, the Th1 cells, the CD8EM IFN-γ positive cells, and the CD8CM IFN-γ positive cells can be used, and more preferably, cell count values of these cells can be used.

Further, based on this result, the inventors of the present invention found that as a method for more quantitatively and accurately determining whether or not to administer an immunosuppressive agent and regulating a dose while monitoring an immune status of a patient after transplant using five markers provided in the present invention, the respective cell count ratios obtained by dividing the cell count values of the above-described five markers, i.e. the Th17 cells, the Treg cells, the Th1 cells, the CD8EM IFN-γ positive cells, and the CD8CM IFN-γ positive cells by the cell count value of the Th17 cells can be used.

This is because the Th17 cells are pathogenic cells that secrete inflammatory cytokine such as IL-17 which is a critical factor in an inflammatory response. Therefore, if cell count ratios of the Treg cells, the Th1 cells, the CD8EM IFN-γ positive cells, and the CD8CM IFN-γ positive cells having an immune regulatory function to the Th17 cells as pathogenic cells in the body of a patient can be quantified, an immune status of the patient can be predicted and determined based on a calculated ratio.

To be more specific, according to an exemplary embodiment of the present invention, as a result of measuring the cell counts of the above-described five markers from blood of a patient in a bad immune status after transplant and in need of being continuously administered with an immunosuppressive agent and respectively dividing the measured cell counts of the markers by the cell count of the Th17 cells as pathogenic cells, Th1/Th17, Treg/Th17, CD8EM IFN-γ/Th17, and CD8CM IFN-γ/Th17 had the respective values of 0.84, 0.43, 0.65, and 0.45 lower than 1 (refer to Table 2).

Further, as a result of measuring the cell counts of the above-described five markers from blood of a patient in a good immune status after transplant and as being allowed to be reduced in a dose of an immunosuppressive agent or allowed not to be administered with the immunosuppressive agent and respectively dividing the measured cell counts of the markers by the cell count of the Th17 cells as pathogenic cells, Th1/Th17, Treg/Th17, CD8EM IFN-γ/Th17, and CD8CM IFN-γ/Th17 had the respective values of 1.71, 2.04, 1.40, and 1.35 higher than 1 (refer to Table 6).

Therefore, from the above results, the inventors of the present invention found that when the respective ratios of the Th1, the Treg, the CD8EM IFN-γ, the CD8CM IFN-γ to the Th17 are lower than 1, an immune status is not good and an immune rejection response occurs, and, thus, it is desirable not to reduce a dose of an immunosuppressive agent as prescription for treating a patient, whereas when the respective ratios of the Th1, the Treg, the CD8EM IFN-γ, the CD8CM IFN-γ to the Th17 are equal to or higher than 1, an immune status can be maintained or regulated to be relatively good, and, thus, the corresponding group can be determined as an immunity resistant group or an immunity stable group which may be allowed to be reduced in a dose of an immunosuppressive agent or allowed not to be administered with the immunosuppressive agent.

Therefore, the present invention can provide a kit for monitoring an immune status after transplant, the kit including a substance for measuring Th17 cells, Treg cells, Th1 cells, CD8EM IFN-γ positive cells, and CD8CM IFN-γ positive cells.

Further, all of the methods known in the art for measuring cell counts of Th17 cells, Treg cells, Th1 cells, CD8EM IFN-γ positive cells, and CD8CM IFN-γ positive cells can be used. Preferably, the measuring may be carried out: for the Th17 cells, by using an antibody to IL-17 to measure an amount of the IL-17; for the Treg cells, by using a Foxp3 antibody to measure an amount of Foxp3; for the Th1 cells, by using an antibody to anti-Human CD4 Percp-Cy7 or anti-human IFN-γ FITC to measure an amount of the IFN-γ of a CD4 T cell; for the CD8EM IFN-γ positive cells, by using an anti-human CD8 APC, anti-human CD45RA FITC, anti-human CCR7, or anti-human IFN-γ PE antibody to measure an amount of IFN-γ of a CD8EM T cell; and for the CD8CM IFN-γ positive cells, by using an anti-human CD8 APC, anti-human CD45RA FITC, anti-human CCR7, or anti-human IFN-γ PE antibody to measure an amount of IFN-γ of a CD8CM T cell.

As the antibody, any of those prepared by injecting a target protein or purchased from the market can be used. The antibody may include a polyclonal antibody, a monoclonal antibody, and a fragment which can be bound to an epitope.

The antibody can be bound to a solid substrate so as to facilitate the subsequent steps such as washing or isolation of a complex. The solid substrate may include, for example, synthetic resins, nitrocellulose, a glass substrate, a metal substrate, a glass fiber, micro-spheres, micro-beads, and the like. Further, the synthetic resins may include polyester, polyvinyl chloride, polystyrene, polypropylene, PVDF, nylon, and the like.

In the kit for monitoring an immune status of the present invention, preferably, the antibody may be bound to a chromogenic enzyme, a chromogenic substance, or a fluorescent molecule, but is not limited thereto. Further, preferably, the antibody may be bound to biotin, or a ligand as a biotin derivative having basically the same binding behavior as biotin with respect to avidin or streptavidin, and preferably, the ligand may be bound to a visualization conjugate bound to the chromogenic enzyme, the chromogenic substance, or the fluorescent molecule which is bound to a ligand-specific binding molecule, but is not limited thereto. The chromogenic enzyme may include, for example, HRP (horseradish peroxidase) or alkaline phosphatase, the chromogenic substance may include coloid gold, and the fluorescent molecule may include FITC (poly L-lysinefluorescein isothiocyanate), RITC (rhodamine-Bisothiocyanate), and the like.

The kit for monitoring an immune status of the present invention can quantitatively or qualitatively analyze a binding reaction through an antigen-antibody reaction or a protein-ligand binding reaction, and, thus, makes it possible to diagnose an immune status after transplant. The binding reaction can be measured by typical methods such as enzyme immunoassay (ELISA), radioimmunoassay (RIA), sandwich assay, western blot, immunoprecipitation, immunohistochemical staining, fluoroimmunoassay, defined substrate technology, antigen-antibody agglutination, and the like.

In the kit, a well plate synthesized from a nitrocellulose film, a PVDF film, a polyvinyl resin or a polystyrene resin, a slide glass made of glass may be used as a support, and a typical color former that makes a color reaction may be preferably used as a chromogenic enzyme, a chromogenic substance, or a fluorescent molecule serving as a marker, fluorescein and dyes such as HRP (horseradish peroxidase), alkaline phosphatase, coloid gold, FITC (poly L-lysinefluorescein isothiocyanate, and RITC (rhodamine-Bisothiocyanate) may be used. In addition, preferably, the kit of the present invention may include a washing solution containing a phosphate buffer solution, NaCl and Tween 20, but is not limited thereto.

Further, the present invention provides a method for monitoring an immune status of an individual after transplant using the above-described five markers for monitoring an immune status as provided in the present invention.

Preferably, the method may include: (a) a step of respectively measuring cell counts of Th17 cells, Treg cells, Th1 cells, CD8EM IFN-γ positive cells, and CD8CM IFN-γ positive cells in peripheral blood of the individual receiving a transplant; and (b) a step of respectively calculating cell count ratios of the Treg cells, the Th1 cells, the CD8EM IFN-γ positive cells, and the CD8CM IFN-γ positive cells to the Th17 cells by respectively dividing the cell count values of the Treg cells, the Th1 cells, the CD8EM IFN-γ positive cells, and the CD8CM IFN-γ positive cells by the cell count value of the Th17 cells.

Furthermore, in the present invention, the immunosuppressive agent may include all of the immunosuppressive agents used in the art, and preferably, a calcineurin inhibitor may be used.

The method for monitoring an immune status of an individual after transplant may further include a step of prescribing a reduced dosage of an immunosuppressive agent to the individual after transplant or determining that the immunosuppressive agent does not need to be administered when each cell count ratio of the Treg cells, the Th1 cells, the CD8EM IFN-γ positive cells, and the CD8CM IFN-γ positive cells to the Th17 cells is equal to or higher than 1. If it is determined that a dosage of the immunosuppressive agent may be reduced, the reduced dosage of the immunosuppressive agent may be in an amount of 75 to 50% based on 100% of an initial dosage of the immunosuppressive agent.

Further, the method may further include a step of determining that a dosage of an immunosuppressive agent to the individual after transplant should not be reduced when each cell count ratio of the Treg cells, the Th1 cells, the CD8EM IFN-γ positive cells, and the CD8CM IFN-γ positive cells to the Th17 cells is lower than 1.

Furthermore, in the present invention, as a marker for monitoring an immune status after transplant, an immune regulatory T cell, i.e. an immune regulatory T lymphocyte (Treg), has been used. The Treg is largely divided into a natural Treg cell and an adaptive Treg cell. A CD4+CD25+T cell as a natural Treg cell is endowed with an immunosuppressive function when it is formed at the thymus and is present at a frequency of 5 to 10% in peripheral CD4+T cells of a normal individual. Although an accurate immunosuppressive mechanism of this cell has not yet been found, it has been found recently that an expression regulator of a Foxp3 gene plays an important role in cell differentiation and cell activity.

Also, a peripheral natural T cell can be differentiated into a cell that has an immunosuppressive effect when stimulated by an autoantigen or an exogenous antigen in a specific environment, which is called adaptive or inducible Treg such as Tr1 that secretes IL-10, Th3 that secretes TGF-β, and CD8 Ts.

Foxp3 is mainly present in a regulatory T cell derived from the thymus, and as a transcriptional factor present in a cell having CD4+CD25+ labelled antigen, it has a function as a suppressor T cell that suppresses formation of IL-2 and cell division with respect to T cells which may potentially cause an autoimmune disease among CD4+CD25-T cells that have a low sensitivity to an indication antigen as an antigen to a T cell expressing Foxp3 and do not express Foxp3 differentiated from the thymus. Further, it is found that Foxp3 with a regulatory T cell expressing Foxp3 has a function of suppressing transcriptional control of not only IL-2 in CD25-T cells through cell-cell contact but also IL-4, IFN-γ, and the like, which are influenced by a transcription factor NFAT.

Therefore, Foxp3-expressing T cells having the above-described function have been used to treat an immune disease by suppressing or regulating an immune reaction, and there have been attempts to apply self-antigen specific T cell clones of human Foxp3-expressing CD4 T cells for cell therapy by treating the clones with a high concentration of IL-2 cytokine and a combination of anti-CD3 and anti-CD28 antibodies to increase the number thereof. Therefore, confirmation of Foxp3 expression becomes a marker for measuring activity or amplification of Treg cells.

Further, the T cells are formed at the human thymus and differentiated into T cells having unique characteristics through a series of differentiation processes. The differentiated T cells are largely divided into type 1 helper T cells (Th1) and type 2 helper T cells (Th2) depending on a function thereof. The Th1 cells secretes interferon gamma and are mainly involved in cell-mediated immunity, and the Th2 cells are involved in humoral immunity. The balance in the immune system is maintained by such two cell groups keeping each other in check so as not to be hyperactivated.

Therefore, it is known that most of the immune diseases are caused by the imbalance between these two immune cells, and, thus, it is important to appropriately maintain the balance between the cells.

Further, Th17 cells have cytotoxicity that maximizes inflammatory signaling and accelerates progression of diseases. Therefore, suppression of differentiation or activation into Th17 cells is one of methods for treating immune diseases. The Th17 cells secrete IL-17. Therefore, a method of suppressing production or secretion of IL-17 of Th17 cells also becomes a method for treating immune diseases.

Accordingly, it can be seen that the present invention can reduce an overdose of an immunosuppressive agent after transplant, can use Th17 cells, Treg cells, Th1 cells, CD8EM IFN-γ positive cells, and CD8CM IFN-γ positive cells as a marker which can be used to monitor an immune status after transplant for managing prognosis after transplant and can be applied to each organ transplant patient, and can also accurately and simply monitor an immune status of a patient by measuring cell counts thereof and calculating ratios of the measured values to a cell count of the Th17 cells.

MODES OF THE INVENTION

Hereinafter, Examples of the present invention will be described in detail.

However, the following Examples are provided just for illustration of the present invention. It is obvious to those of ordinary skill in the art that the scope of the present invention is not limited to these Examples.

Example 1

Confirmation of Immune Status Depending on Change in Dose of Immunosuppressive Agent to Organ Transplant Patient The following experiments were carried out with the consent of the patients undergoing a liver transplant at Seoul St. Mary's Hospital of the Catholic University of Korea. The patients who agreed with the experiments had undergone a liver transplant five years ago. While reducing a dose of an immunosuppressive agent, we measured the intracellular level of Th17 (CD4+IL-17+), Treg(CD4+CD25highFoxp3+), Th1(CD4+IFN-γ), CD8EM IFN-γ+ (CD8+CD45RA-CCR7-IFN-γ+), and CD8CM IFN-γ+ (CD8+CD45RA-CCR7+IFN-γ+). Further, the experiments were carried out to the patient group in the case of taking 100% of calcineurin inhibitor (CNI) as an immunosuppressive agent (taking 100 mg of cyclosporine A), in the case of taking a dose reduced to 75%, and in the case of taking a dose reduced to 50%. The experiments were carried out to each of the samples obtained from the patient group in a good immune status and the patient group in a bad immune status.

<1-1> Measurement of ALT and ALP in Serum

Blood was collected from the patients who agreed with the experiments, and then, a Hitachi 7600-210 was used to measure ALT and ALP in the blood.

<1-2> Measurement of Th1 and Th17 Cells

When 100%, 75%, and 50% of the immunosuppressive agent was administered to the peripheral blood obtained from the patients involved in the experiment of Example <1-1>, heparin-treated tubes were used to collect blood by venipuncture and peripheral blood mononuclear cells (PBMC) were separated with a Ficoll Paque TM as a centrifuge using a specific gravity difference. Then, in order to measure IFN-γ and IL-17 of cells expressing IFN-γ (a marker indicating a Th1 cell) and IL-17 (a marker indicating a Th17 cell) from CD4 T cells, a 48-well plate was used to process $5 \times 10^5$ cells with 50 ng/ml of PMA, 500 ng/ml of ionomycin, and 0.67 μl/$1 \times 10^6$ of golgistop at the same time and then culture the cells for 4 hours to stimulate the cells. Then, CD4 PECY7 antibodies were added to the collected cells and reacted at 4° C. under a dark condition, and then washed with FACs buffer (0.002% sodium azide and 0.2% BSA/PBS). These cells were reacted with cytofix/cytoperm for 30 minutes and then washed with perm wash. Then, the cells were reacted again with IFN-γ FITC and IL-17 PE antibodies for 30 minutes under a dark condition, and then washed with perm wash and re-suspended in the FACs buffer. Then, the cells were analyzed by flow cytometry.

<1-3> Measurement of Treg Cells

Peripheral blood mononuclear cells were obtained by the same method as used in Example <1-2>, and CD4 PE CY 7+CD25APC antibodies were added thereto in order to measure CD4+CD25highFoxp3+Treg cells and reacted at 4° C. under a dark condition, and then washed with FACs buffer (0.002% sodium azide and 0.2% BSA/PBS). Then, these cells were additionally reacted with cytofix/cytoperm dedicated to Treg for 30 minutes. Then, the cells were washed with perm wash dedicated to Treg and reacted with Foxp3 antibodies for 30 minutes under a dark condition, and then washed with perm wash dedicated to Treg and re-suspended in the FACs buffer. Then, the cells were analyzed by flow cytometry.

<1-4> Measurement of CD8+CM IFN-γ+, CD8+EM IFN-γ+Cells

Peripheral blood mononuclear cells were obtained by the same method as used in Example <1-2>, a 48-well plate was used to process $5 \times 10^5$ cells with 25 ng/ml of PMA, 250 ng/ml of ionomycin, and 0.67 μl/$1 \times 10^6$ of golgistop at the same time and then culture the cells for 4 hours to stimulate the cells. Then, CD8APC, CD45RA FITC, and CCR7 Percp antibodies were added to the collected cells and reacted at 4° C. under a dark condition, and then washed with FACs buffer (0.002% sodium azide and 0.2% BSA/PBS). These cells were reacted with cytofix/cytoperm for 30 minutes and then washed with perm wash. Then, the cells were reacted again with IFN-γ PE antibodies for 30 minutes under a dark condition, and then washed with perm wash and re-suspended in the FACs buffer. Then, the cells were analyzed by flow cytometry.

<1-5> Result of Experiment

Figure 2:
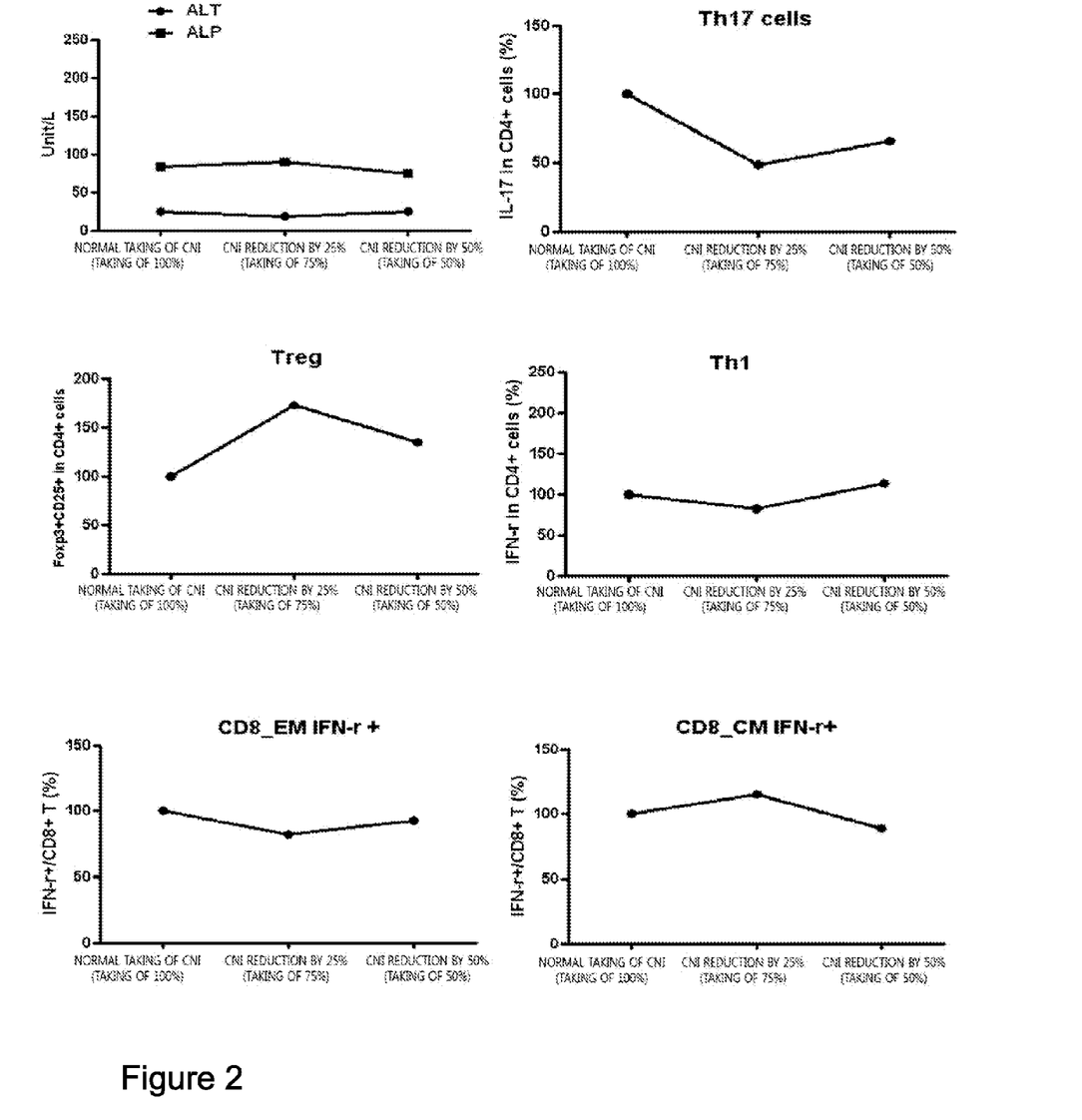
FIG. 2 is a graph illustrating changes in cell counts of Th17 cells, Treg cells, Th1 cells, CD8EM IFN-γ positive cells, and CD8CM IFN-γ positive cells measured while a dosage of an immunosuppressive agent to be administered to a mononuclear cell in peripheral blood obtained from a patient in a good immune status among liver transplant patients according to an exemplary embodiment of the present invention.

The results obtained from the experiments according to Examples <1-1> to <1-4> were as illustrated in FIG. 1 to FIG. 3. Firstly, according to the result as illustrated in FIG. 1, in the patient in a bad immune status after transplant, as an amount of the immunosuppressive agent decreased, ALT and ALP as markers of liver injury increased and inflammatory Th17 cells also increased. However, Treg(CD4+CD25highFoxp3+), Th1(CD4+IFN-γ), CD8EM IFN-γ+ (CD8+CD45RA-CCR7-IFN-γ+), and CD8CM IFN-γ+

(CD8+CD45RA-CCR7+IFN-γ+) cells having an immune regulatory function decreased (refer to FIG. 1).

Thus, the inventors of the present invention examined whether or not an immune reaction is recovered when a dose of the immunosuppressive agent is increased again with respect to the above result caused by a reduction in the immunosuppressive agent in the group in a bad immune status. As illustrated in FIG. 3, in the case of reducing a dose of the immunosuppressive agent to 50% and then increasing a dose of the immunosuppressive agent to 75%, ALT and ALP values and a value of the inflammatory Th17 cells decreased, whereas Treg(CD4+CD25highFoxp3+), Th1 (CD4+IFN-γ), CD8EM IFN-γ+(CD8+CD45RA-CCR7-IFN-γ+), and CD8CM IFN-γ+(CD8+CD45RA-CCR7+IFN-γ+) increased again.

Therefore, it could be seen that it is necessary to continuously administer the immunosuppressive agent to this patient group without reduction in this case.

Further, according to the result of the experiment carried out to the patient group in a good immune status after transplant, as illustrated in FIG. 2, even when a dose of the immunosuppressive agent was reduced to 50%, ALT and ALP values were nearly equal to those in the case of administering 100% of the immunosuppressive agent and a value of Th17 cell was not much different from that of the group administered with 75% of the immunosuppressive agent. Further, values of Treg(CD4+CD25highFoxp3+), Th1(CD4+IFN-γ), CD8EM IFN-γ+(CD8+CD45RA-CCR7-IFN-γ+), and CD8CM IFN-γ+(CD8+CD45RA-CCR7+IFN-γ+) were not much different from those of the group administered with 75% of the immunosuppressive agent.

Example 2

Measurement of Variation of Cells to be Monitored of the Present Invention Depending on Amount of Immunosuppressive Agent With respect to the results obtained from the experiments according to Examples <1-1> to <1-4>, variations of Th17 (CD4+IL-17+), Treg(CD4+CD25highFoxp3+), Th1(CD4+IFN-γ), CD8EM IFN-γ+(CD8+CD45RA-CCR7-IFN-γ+), and CD8CM IFN-γ+(CD8+CD45RA-CCR7+IFN-γ+) were measured using samples obtained by varying a dose of the immunosuppressive agent to each of the group in a bad immune status and the group in a good immune status and digitized to compare values of the experimental groups. That is, a value of 100% was determined based on 100% of the immunosuppressive agent to the respective markers (Th1, Th17, Treg, CD8EM IFN-γ, and CD8CM IFN-γ) without reduction in the immunosuppressive agent, quantitative values were obtained based on change ratios of Th17, Treg, Th1, CD8EM IFN-γ+, and CD8CM IFN-γ+ caused by a reduction in drug and listed in the following Table 1 (for example, in the case of taking 100% of the immunosuppressive agent, when a value of Th17 cells is 0.75, this value is set to 100, and in the case of taking 75% of the immunosuppressive agent, when a value of -Th17 cells is 0.90, this value is set to 120). Further, the ratios of the respective markers were divided by the value of Th17 as a critical factor in an inflammatory response to express variations of the four markers depending on the value of Th17 as ratios. The more detailed results of the experiments were as listed in the following tables.

TABLE 1

Results of value variations of five markers in the patient group in a bad immune status

| | Taking of 100% immunosuppressive agent | Taking of 75% immunosuppressive agent | Taking of 50% immunosuppressive agent |
|---|---|---|---|
| Th17 | 100 | 54.5 | 113.6 |
| Th1 | 100 | 179.9 | 96.0 |
| Treg | 100 | 135.5 | 49.2 |
| CD8EM IFN-γ | 100 | 106.2 | 74.2 |
| CD8CM IFN-γ | 100 | 93.9 | 51.3 |

TABLE 2

Values obtained by dividing the values of respective markers in Table 1 by the value of Th17

| | Taking of 100% | Taking of 75% | Taking of 50% |
|---|---|---|---|
| Th1/Th17 | 1 | 3.30 | 0.84 |
| Treg/Th17 | 1 | 2.48 | 0.43 |
| CD8EM IFN-γ/Th17 | 1 | 1.95 | 0.65 |
| CD8CM IFN-γ/Th17 | 1 | 1.72 | 0.45 |

TABLE 3

Results of value variations of five markers in the patient group in a bad immune status when a dose of the immunosuppressive agent is reduced to 50% and then increased to 75%

| | Taking of 100% | Taking of 75% | Taking of 50% | Taking of 75% |
|---|---|---|---|---|
| Th17 | 100 | 54.5 | 113.6 | 68.2 |
| Th1 | 100 | 179.9 | 96.0 | 228.5 |
| Treg | 100 | 135.5 | 49.2 | 16.0 |
| CD8EM IFN-γ | 100 | 106.2 | 74.2 | 140.6 |
| CD8CM IFN-γ | 100 | 93.9 | 51.3 | 97.8 |

TABLE 4

Values obtained by dividing the values of respective markers in Table 3 by the value of Th17

| | Taking of 100% | Taking of 75% | Taking of 50% | Taking of 75% |
|---|---|---|---|---|
| Th1/Th17 | 1 | 3.30 | 0.84 | 3.35 |
| Treg/Th17 | 1 | 2.48 | 0.43 | 2.36 |
| CD8EM IFN-γ/Th17 | 1 | 1.95 | 0.65 | 2.06 |
| CD8CM IFN-γ/Th17 | 1 | 1.72 | 0.45 | 1.43 |

TABLE 5

Results of value variations of five markers in the patient group in a good immune status

| | Taking of 100% immunosuppressive agent | Taking of 75% immunosuppressive agent | Taking of 50% immunosuppressive agent |
|---|---|---|---|
| Th17 | 100 | 48.5 | 66.0 |
| Th1 | 100 | 82.1 | 113.0 |

TABLE 5-continued

Results of value variations of five markers in the patient group in a good immune status

|  | Taking of 100% immunosuppressive agent | Taking of 75% immunosuppressive agent | Taking of 50% immunosuppressive agent |
|---|---|---|---|
| Treg | 100 | 173.1 | 134.8 |
| CD8EM IFN-γ | 100 | 82.5 | 92.5 |
| CD8CM IFN-γ | 100 | 115.0 | 88.8 |

TABLE 6

Values obtained by dividing the values of respective markers in Table 5 by the value of Th17

|  | Taking of 100% | Taking of 75% | Taking of 50% |
|---|---|---|---|
| Th1/Th17 | 1 | 1.69 | 1.71 |
| Treg/Th17 | 1 | 3.57 | 2.04 |
| CD8EM IFN-γ/Th17 | 1 | 1.70 | 1.40 |
| CD8CM IFN-γ/Th17 | 1 | 2.37 | 1.35 |

According to the analysis result, as listed in Table 1 to Table 4, it could be seen that when each ratio of Treg, Th1, CD8EM IFN-γ, and CD8CM IFN-γ to Th17 was lower than 1, an immune status was not good and an immune rejection response occurred. It could be seen that it is desirable not to reduce a dose of the immunosuppressive agent as prescription for treating a patient in this case.

On the other hand, as listed in Table 5 and Table 6, it could be seen that when each ratio of Treg, Th1, CD8EM IFN-γ, and CD8CM IFN-γ to Th17 was equal to or higher than 1, an immune status can be maintained or regulated to be relatively good in spite of a reduction in the immunosuppressive agent. Therefore, it could be seen that the corresponding group can be determined as an immunity resistant group or an immunity stable group which may be allowed to be reduced in a dose of the immunosuppressive agent in this case.

Consequently, as exhibited from the experimental results, it could be seen that by measuring values of the five markers, i.e. Th1, Th17, Treg, CD8EM IFN-γ, and CD8CM IFN-γ provided by the present invention, it is possible to monitor an immune status of a patient for a treatment with an immunosuppressive agent to an immune rejection response occurring during a transplant operation so as to determine an amount and a dose of the immunosuppressive agent and whether or not to administer the immunosuppressive agent.

While the present invention has been exhibited and described with reference to preferable Examples thereof, it will be understood by those skilled in the art that various changes in form and details may be made therein without departing from the spirit and scope of the present invention as defined by the appended claims. Therefore, the disclosed Examples should not be considered in view of explanation, but no limitation. The technical scope of the present invention is taught in the claims, but not the detailed description, and all the differences in the equivalent scope thereof should be construed as falling within the present invention.

The invention claimed is:

1. A kit for monitoring immune status after transplant consisting of
antibody to IL17 (interleukin-17) for measuring Th17 (T helper 17 cell);
antibody to Foxp3 for measuring Trees cell (regulatory T cell);
antibody to IFN(interferon)-gamma for measuring the Th1 (T helper 1 cell);
anti-human CD8 APC (CD8 allophycocyanin) for measuring the CD8EM (CD8 effector memory) interferon-gamma positive T cell and CD8CM (CD8 central memory) interferon-gamma positive T cell;
anti-human CD45RA FITC (fluorescein isothiocyanate) for measuring CD8EM interferon-gamma positive T cell and CD8CM interferon-gamma positive T cell;
anti-human CCR7 (C-C chemokine receptor type 7) PerCP (peridinin chlorophyll) for measuring CD8EM interferon-gamma positive T cell and CD8CM interferon-gamma positive T cell; and
anti-human IFN (interferon)-gamma PE (phycoerythrin) antibody for measuring CD8EM interferon-gamma positive T cell and CD8CM interferon-gamma positive T cell.

* * * * *